United States Patent [19]

Ganguly et al.

[11] Patent Number: 4,622,314

[45] Date of Patent: Nov. 11, 1986

[54] SUBSTITUTED OLIGOSACCHARIDE ANTIBIOTICS

[75] Inventors: Ashit K. Ganguly, Upper Montclair; Olga Sarre, Verona; Viyyoor M. Girijavallabhan, Parsippany, all of N.J.

[73] Assignee: Schering Corporation, Kenilworth, N.J.

[21] Appl. No.: 787,405

[22] Filed: Oct. 15, 1985

[51] Int. Cl.[4] .................. A61K 31/73; C07H 5/04; C08B 37/00
[52] U.S. Cl. .................. 514/54; 536/16.8; 536/18.1
[58] Field of Search ............... 514/54; 536/18.1, 16.8

[56] References Cited

U.S. PATENT DOCUMENTS 4,264,591   4/1981   Bauer et al. .................. 514/54

Primary Examiner—Johnnie R. Brown
Attorney, Agent, or Firm—Thomas D. Hoffman; Gerald S. Rosen; Stephen I. Miller

[57] ABSTRACT

There is disclosed desevernitrose, acetamido, ethylamino and diethylamino derivatives of antibiotic 13-384 components 1 and 5 represented by the following formula

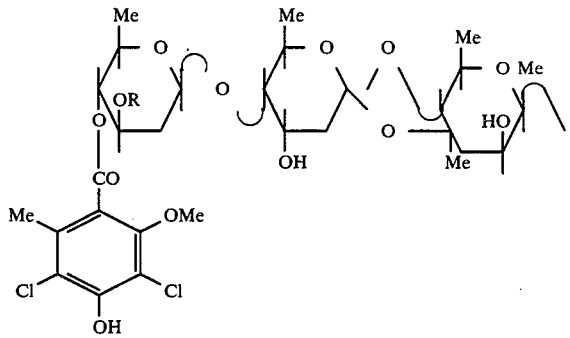

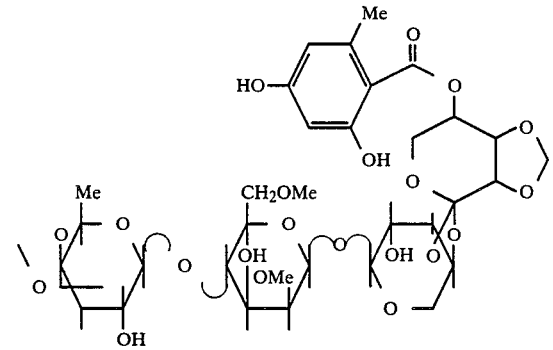

wherein R is hydrogen, or

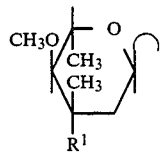

wherein $R^1$ is acetamide, ethylamine, diethylamine, N-hydroxylamino, nitroso or the pharmaceutically acceptable salts thereof.

15 Claims, No Drawings

SUBSTITUTED OLIGOSACCHARIDE ANTIBIOTICS

BACKGROUND OF THE INVENTION

This invention relates to antibacterially active derivatives of an antibiotic complex produced by *Micromonospora carbonacea var africana var nov.* NRRL 15099, ATCC 39149, which is designated antibiotic 13-384 in commonly assigned U.S. patent application Ser. No. 623,266, filed June 21, 1984, which application is incorporated herein by reference. This complex, the method of producing and isolating it, its components 1 and 5 and their use as antibacterial agents are disclosed, in said patent application. More specifically, this invention relates to derivatives of the components of the complex designated components 1 and 5 of antibiotic 13-384 and their antibacterial compositions, as well as methods of treating antibacterial infections therewith.

SUMMARY OF THE INVENTION

The present invention is directed to the desevernitrose, acetamido, ethylamino and diethylamino derivatives of antibiotic 13-384 components 1 and 5, represented by the following Formula I

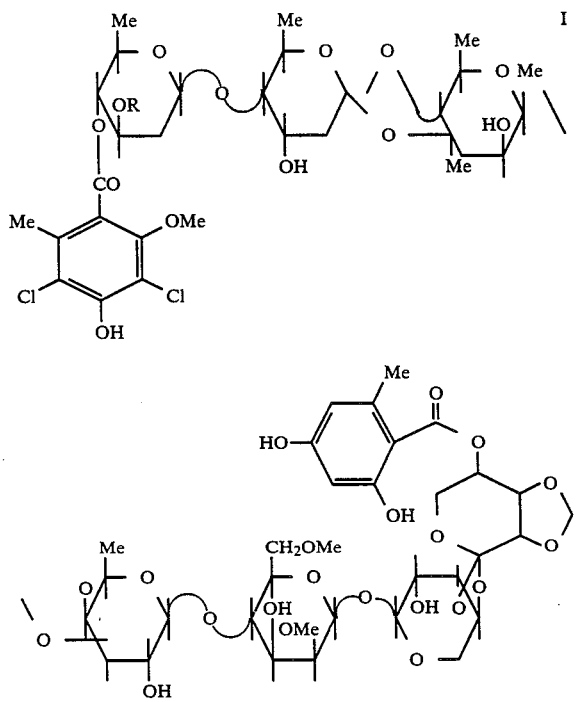

wherein R is hydrogen, or

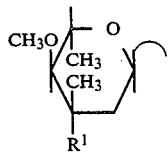

wherein $R^1$ is acetamido; ethylamino, or diethylamino, N-hydroxylamino, nitroso or the pharmaceutically acceptable salts thereof.

The pharmaceutically acceptable salts of the compounds of formula I are the alkali metal and alkaline-earth metal salts thereof. Representative salts are the lithium, sodium, potassium, barium, strontium, and calcium salts, preferred are sodium salts.

The compounds of this invention possess antibacterial activity against both gram-positive and gram-negative bacteria. Generally, the compounds of this invention show advantageous activity against methicillin resistant *Staphlococcus aureus.*

Anti-bacterial in vitro activity was also observed against various species of Streptococcus with Minimum Inhibitory Concentrations (MIC's) ranging from 0.006 mcg/ml to 16.0 mcg/ml.

Most importantly, the compounds of this invention are injectable antibacterial agents which afford good blood levels at antibacterial dosages.

The present invention also includes within its scope pharmaceutical compositions comprising an antibacterially effective amount of a compound of formula I together with a compatible pharmaceutically acceptable carrier. The compounds of formula I may be the only antibacterial agent in the pharmaceutical dosage forms, or may be admixed with other compatible antibacterial agents.

Also contemplated by this invention is the method of effectively treating a warm-blooded animal having a susceptible bacterial infection which comprises administering to said animal an antibacterially effective amount of a compound of formula I.

DESCRIPTION OF THE INVENTION

The N,N-diethylamino derivative of antibiotic 13-384, component 5 may be prepared by the reduction of the component and acetaldehyde in an inert organic solvent, e.g. 2-methoxyethanol, dimethoxyethane, 2-methoxyethylether or a lower alkanol, preferably 2-methoxyethanol. The reduction is conducted under pressure in an atmosphere of hydrogen, in the presence of an alkali metal carbonate or bicarbonate, preferably sodium bicarbonate, and platinum oxide as a reducing catalyst, until the reaction is complete, usually about 24 to 48 hours. The pressure used is about 20-30 psi, preferably 25 psi. The product is then recovered using chromatography.

The N-ethyl derivatives may be prepared following the above procedure by using Raney Nickel catalyst instead of platinum oxide.

The desevernitrose derivative of antibiotic 13-384, component 1, may be prepared by the following sequence of reactions, (a) reduction of 13-384 component 1 to the hydroxylamino derivative (b) oxidation of the hydroxylamino 13-384 to the nitroso derivative (c) reaction of the nitroso compound with phosphites or phosphines. The reduction of 13-384 component 1 is carried out in an inert organic solvent e.g. tetrahydrofuran, dioxane, dimethoxyethane or 2-methoxyethylether in the presence of a catalyst e.g. sodium amalgam, zinc-copper complex or zinc powder with a proton source e.g. ammonium chloride, tartaric acid or ammonium carbonate. The reaction is conducted under an inert atmosphere, e.g. nitrogen at room temperature for a time sufficient to produce the N-hydroxylamino derivative, e.g. about 24 to 48 hours. The product is then recovered.

The N-hydroxylamino derivative is then reacted with activated carbon in an inert organic solvent, e.g. methanol, ethanol or other lower alkanols for a time sufficient to complete the reaction, about 5 to 10 hours, to give the nitroso derivative. The product is separated from the activated carbon and recovered.

The nitroso product is reacted under an inert atmosphere e.g. nitrogen with an alkoxy phosphorous compound e.g. triethyl phosphite, tributylphosphite, or arylphosphines e.g. triphenyl phosphine in an inert organic solvent e.g. tetrahydrofuran, dioxane, dimethoxyethane, or 2-methoxyethyl ether. The solution is heated until the reaction is complete. The residue is recovered to give the desevernitrose derivative of antibiotic 13-384, component 1.

The acetamido derivative of antibiotic 13-384, component 5 may be prepared by the reaction of the component with acetic anhydride in an inert organic solvent e.g. tetrahydrofuran, dioxane, dimethoxyethane or a lower alkanol at room temperature e.g. about 25° C. for, about 3 hours. The progress of the reaction is monitored by thin layer chromatography (TLC). The resulting product, the acetamido derivative of antibiotic 13-384, component 5, is then recovered.

Conversion of component 1 to component 5 can be by reduction of component 1 in the presence of active Raney Nickel in an inert organic solvent such as ethyl acetate, tetrahydrofuran, methoxyethanol, or ethanol, at 35 psi for 21 hours.

This conversion can also be accomplished by hydrogenating component 1 in the presence of aluminum-mercury amalgam in ethanol or tetrahydrofuran-ethanol mixture. The corresponding derivatives of components 1 and 5 can be made by using component 5 in place of component 1 as described herein and vice versa.

Preparation of the pharmaceutically acceptable salts of compounds of formula I may be carried out according to conventional procedures for forming salts. Salts can be formed, for example, by treating with metal hydroxide compounds such as sodium hydroxide, calcium or magnesium hydroxide, or with ammonia or a suitable organic amine, wherein preferably stoichiometric amounts or only a small excess of the salt-forming agent is used. Acid addition salts are obtained in the usual manner, for example, by treating with an acid or a suitable anion exchange reagent.

The antibiotics of the invention may be combined with any suitable pharmaceutical carrier and administered orally, parenterally or topically in a variety of formulations. For oral administration, the antibiotics of this invention may be compounded in the form of tablets, capsules, elixirs or the like. Tablets and capsules may contain such excipients as starch or lactose; liquid forms may contain coloring or flavoring agents. Topical preparations may be in the form of creams, hydrophobic and hydrophilic ointments, or aqueous, non-aqueous or emulsion-type lotions. Typical carriers for such formulations are water, oils, greases polyesters and polyols. Parenteral formulations, e.g., injectable dosage forms, are usually liquids such as solutions or suspensions, with typical carriers being distilled water and saline solution.

Typical pharmaceutically carriers for use in the pharmaceutical formulations of the compounds of this invention are exemplified by sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn set; non-ionic, cationic and anonic surfactants, ethylene glycol polymers; betacyclodextrin; fatty acids, hydrolyzed cereal solids; water; polyalkylene glycols; gums; and petroleum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dose to be administered in any particular dosage form will depend upon various factors, such as the susceptibility of the infecting organism to the antibiotic, the stage and severity of the infection. Generally, the dosage administered is from about 1.0 mg to about 25 mg per kilogram of body weight per day, in divided dosages, the specified dosage being left to the discretion of the practitioner. In treating certain patients with the compounds of this invention, it is possible to include other pharmaceutically active ingredients in the same dosage unit.

The following examples illustrate the preparations of the compounds of the present invention, wherein the structure of the compounds were verified by Proton Magnetic Resonance; $C^{13}$ Magnetic Resonance, and High Resolution Mass Spectrometry e.g. F.A.B.

EXAMPLE I

N,N-DIETHYLAMINO-13-384-COMPONENT 5

A solution of 200 mg of 13-384, component 5, as isolated and purified in U.S. patent application Ser. No. 623,266, filed June 21, 1984, in 8 ml of 2-methoxyethanol and 2 ml of freshly distilled acetaldehyde was stirred under hydrogen in the presence of 40 mg of sodium bicarbonate and 200 mg of platinum oxide at 25 psi for 48 hours. The catalyst was filtered off and the filtrate concentrated to dryness, under vacuum, to yield crude title compound. Chromatography on a silica gel column, eluting with 5% v/v of methanol in chloroform, yielded pure title compound. $C_{74}H_{107}O_{36}NCl_2$; $M+1655$; $[\alpha]_D^{26}$-45.9° (MeOH); $\delta$ 119.357 and $\delta$ 120.529 (Ortho Esters).

The N,N-diethylamino-13-384-Component-1 derivative can be made by substituting Component 1 for Component 5 in the above example.

EXAMPLE II

N-ETHYLAMINO-13-384-COMPONENT 5

A solution of 150 mg of 13-384, component 5 as isolated and purified in U.S. patent application Ser. No. 623,266, filed June 21, 1984 in 3 ml of methanol and 3 ml of freshly distilled acetaldehyde was stirred under hydrogen in the presence of 35 mg of sodium bicarbonate and Raney nickel (about 1.5 ml) at 25 psi for 48 hours. The catalyst was filtered off and the solvent was removed under reduced pressure to yield the title compound. Chromatography on a silica gel column, eluting with 10% v/v of methanol in chloroform, yielded pure title compound. $C_{72}H_{103}O_{36}NCl_2$; $M+1627$; $[\alpha]_D^{26}$-45.3° (MeOH); $\delta$ 119.277 and $\delta$ 120.488 (Ortho Esters).

The N-ethylamino-13-384-Component 5 derivative can also be made by reducing Component 1 to Component 5 then following the above example.

EXAMPLE III

DESEVERNITROSE-13-384-COMPONENT 1

(a) N-HYDROXYLAMINO-13-384-COMPONENT-1

To a solution of 1.0 g of 13-384 component 1, as isolated and purified in U.S. patent application Ser. No. 623,266, filed June 21, 1984, in 30 ml of peroxide free tetrahydrofuran (THF) was added 600 mg of zinc powder. To the stirring slurry was added, dropwise, 2 ml of a 10% aqueous solution of ammonium chloride. The suspension was stirred under nitrogen at room temperature for 35 minutes. The progress of the reaction was monitored by TLC using 8% v/v methanol in chloroform as eluent. The filtered reaction mixture was washed twice with brine solution. The organic layer was dried over anhydrous sodium sulfate and concentrated under reduced pressure to yield the title compound.

(b) NITROSO-13-384-COMPONENT-1

To a solution of 960 mg of crude hydroxylamino-13-384, component 1, in 30 ml of methanol was added 2 g of "NUCHAR" 12×40 mesh active carbon (Westvaco Chemical Division). The suspension was stirred at room temperature for 7 hours. The progress of the reaction was followed by TLC using 8% v/v methanol in chloroform as eluent. The "NUCHAR" was filtered off on a buchner funnel using a filter pad, and thoroughly washed with methanol. The clear filtrate was concentrated to dryness under reduced pressure. The "NUCHAR" was further extracted with tetrahydrofuran to give crude title compound.

(c) DESEVERNITROSE-13-384-COMPONENT-1

Under nitrogen atmosphere, to a solution of 500 mg of crude nitroso-13-384, component 1, in 16 ml of peroxide free dioxane was added 1.6 ml of triethylphosphite. The reaction solution was heated in a 100° C. oil bath, with stirring, until TLC analysis indicated the absence of starting compound (about 2 hours). The reaction mixture was evaporated to a residue under vacuum. The residue was dissolved in a minimal amount of tetrahydrofuran and slowly precipitated with hexane. The precipitate was filtered and thoroughly washed with hexane. The crude title compound was chromatographed through a silica gel column, eluting with 3% v/v of methanol in chloroform, to give pure title compound, which may be further purified by crystallization from acetone. $C_{62}H_{84}O_{34}Cl_2$; M.P. 198°–202° C.; M+1442; $[\alpha]_D^{26}$-20.7° (MeOH),

EXAMPLE IV

ACETAMIDO-13-384-COMPONENT-5

To a solution of 200 mg of antibiotic 13-384, component 5, in 13 ml of peroxide free tetrahydrofuran was added 85 mg of sodium bicarbonate and 0.1 ml of acetic anhydride. The reaction mixture was stirred at room temperature until TLC analysis, in 18% v/v of methanol in chloroform, indicated the absence of starting compound (about 3 hours). The reaction mixture was filtered and the clear filtrate was concentrated to a residue under reduced pressure. Titration of the residue gave solids of crude multiacetylated 13-384, component 5. The solids were dissolved in 2.5 ml of 5% ammonium hydroxide in methanol and allowed to stand at room temperature for about 40 minutes. The progress of the reaction was monitored by TLC, using 10% v/v of methanol in chloroform. The reaction solution was concentrated to a low volume, under reduced pressure, diluted with ethyl acetate and again concentrated to a lower volume. The residue was then partitioned between ethylacetate and water, and separated. The aqueous portion was extracted with ethylacetate. The combined ethylacetate extracts were washed once with brine, dried over sodium sulfate, and evaporated to a residue, under reduced pressure, to give crude title compound. Chromatography of the crude title compound on four preparative thin layer silica gel plates (1,000 microns thick) using 10% v/v of methanol in chloroform as eluant, and extraction of the product off of the silica gel with distilled tetrahydrofuran gave the title compound. $C_{72}H_{101}O_{37}NCl_2$; M+1641; $[\alpha]_D^{26}$-47.3° (MeOH).

Acetamido-13-384-Component 5 can also be made from Component 1 by reduction to Component 5 followed by acetylation as in the above example.

Antibacterial properties of the compounds of this invention were determined by both in-vitro and in-vivo tests against a variety of gram-positive and gram-negative organisms. In-vitro antibacterial activity tests were performed via conventional agar dilution methods in Mueller-Hinton agar (MHA).

We claim:

1. A compound represented by the formula

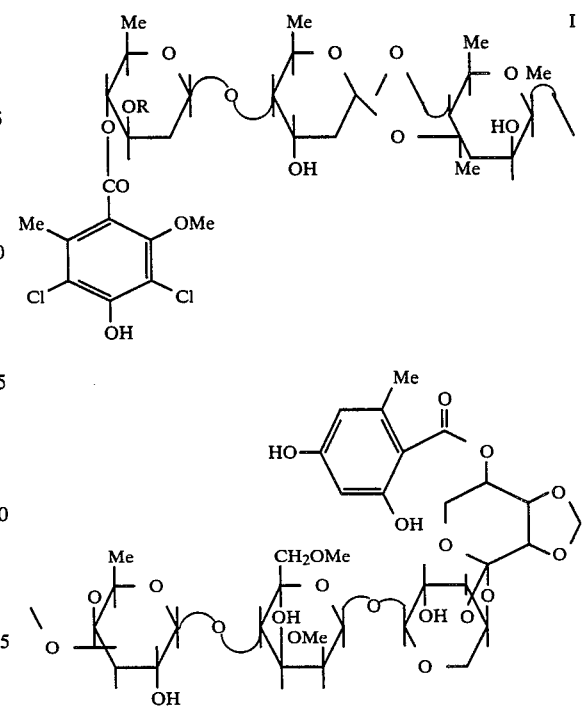

wherein R is hydrogen, or

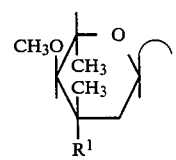

wherein $R^1$ is acetamido; ethylamino; or diethylamino; N hydroxylamino; nitroso or the pharmaceutically acceptable salts thereof.

2. A compound as defined in claim 1, wherein $R^1$ is N-hydroxylamino.

3. A compound as defined in claim 1, wherein $R^1$ is nitroso.

4. A compound as defined in claim 1, wherein R is hydrogen.

5. A compound as defined in claim 1, wherein $R^1$ is acetamido.

6. A compound as defined in claim 1, wherein $R^1$ is ethylamino.

7. A compound as defined in claim 1, wherein $R^1$ is diethylamino.

8. An antibacterial composition comprising a compound as defined in claim 1 in an amount sufficient to elicit antibacterial activity against susceptible gram-positive and gram-negative bacteria, together with a pharmaceutically acceptable carrier.

9. A method of eliciting an antibacterial effect in a warm-blooded animal having a susceptible gram-positive or gram-negative bacterial infection which comprises administering to said animal an antibacterially effective amount of a compound represented by the formula

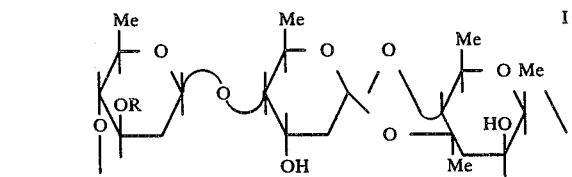
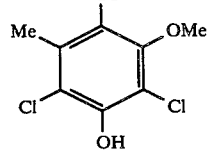
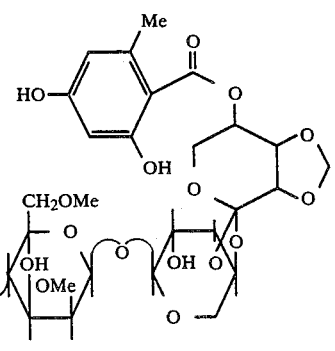

wherein R is hydrogen, or

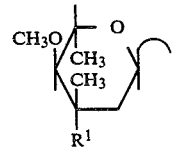

wherein $R^1$ is acetamido; ethylamino; or diethylamino; N hydroxylamino; nitroso or the pharmaceutically acceptable salts thereof.

10. The method of claim 9 wherein $R^1$ is N-hydroxylamino.

11. The method of claim 9 wherein $R^1$ is nitroso.

12. The method of claim 9 wherein R is hydrogen.

13. The method of claim 9 wherein $R^1$ is acetamido.

14. The method of claim 9 wherein $R^1$ is ethylamino.

15. The method of claim 9 wherein $R^1$ is diethylamino.

* * * * *